United States Patent
Stopperan et al.

(10) Patent No.: US 7,309,010 B2
(45) Date of Patent: Dec. 18, 2007

(54) IDENTIFICATION METHOD AND APPARATUS

(75) Inventors: William I. Stopperan, Windsor, CO (US); Troy M. Bryan, Bridgeport, NE (US)

(73) Assignee: Western Pathology Consultants, Inc., Scottsbluff, NE (US)

( * ) Notice: Subject to any disclaimer, the term of this patent is extended or adjusted under 35 U.S.C. 154(b) by 636 days.

(21) Appl. No.: 10/701,660

(22) Filed: Nov. 4, 2003

(65) Prior Publication Data

US 2004/0117060 A1 Jun. 17, 2004

Related U.S. Application Data

(60) Provisional application No. 60/423,955, filed on Nov. 4, 2002.

(51) Int. Cl.
 *G06F 19/00* (2006.01)
 *G06Q 30/00* (2006.01)
 *G06Q 90/00* (2006.01)

(52) U.S. Cl. ............ 235/385; 235/487; 705/22

(58) Field of Classification Search ........... 235/385, 235/375–377, 487, 438, 378, 485; 436/43, 436/46; 705/22, 28; 435/43, 46
See application file for complete search history.

(56) References Cited

U.S. PATENT DOCUMENTS

| | | | | |
|---|---|---|---|---|
| 4,871,077 A * | 10/1989 | Ogden et al. | ............... | 215/365 |
| 5,775,735 A | 7/1998 | Bolnick et al. | ............... | 283/81 |
| 5,855,395 A | 1/1999 | Foote et al. | ............... | 283/67 |
| 5,902,982 A | 5/1999 | Lappe | ............... | 235/375 |
| 5,916,815 A | 6/1999 | Lappe | ............... | 436/92 |
| 5,929,422 A | 7/1999 | Lappe | ............... | 235/462.13 |
| 6,036,092 A | 3/2000 | Lappe | ............... | 235/462.13 |
| 6,055,487 A | 4/2000 | Margery et al. | ............... | 702/84 |
| 6,158,779 A | 12/2000 | Petrick | ............... | 283/81 |
| 6,342,183 B1 | 1/2002 | Lappe et al. | ............... | 422/58 |
| 6,376,251 B1 | 4/2002 | Braun et al. | ............... | 436/43 |
| 6,394,354 B1 | 5/2002 | Wilz, Sr. et al. | ............... | 235/472.01 |
| 6,581,012 B1 * | 6/2003 | Aryev et al. | ............... | 702/22 |
| 6,598,796 B2 * | 7/2003 | Harrop | ............... | 235/462.01 |
| 6,832,722 B1 * | 12/2004 | Cocola et al. | ............... | 235/385 |
| 6,983,884 B2 * | 1/2006 | Auchinleck | ............... | 235/385 |
| 2003/0059347 A1 * | 3/2003 | Ostgaard et al. | ............... | 422/102 |

(Continued)

OTHER PUBLICATIONS

"eScreen: The complete drug screening system", eScreen, Inc., 2 pages.

(Continued)

*Primary Examiner*—Thien M. Le
*Assistant Examiner*—Edwyn Labaze
(74) *Attorney, Agent, or Firm*—Santangelo Law Offices, P.C.

(57) ABSTRACT

At least one embodiment of the inventive technology focuses on new methods and apparatus relative to generation of a custody and control form that finds application in drug use or clinical testing, among other fields. At least one embodiment of another aspect of the inventive technology focuses on methods and apparatus relative to an encrypted, character-based identifier usable to adequately identify an event (a purchase, e.g.), an object (a product purchased, e.g.) or substance (a specimen collected from an individual for drug testing or clinical testing); in a preferred embodiment, this identifier is based on a time and entity associated with the event, object or substance to be identified.

38 Claims, 1 Drawing Sheet

U.S. PATENT DOCUMENTS

2003/0183683 A1* 10/2003 Stewart .................. 235/376
2004/0033501 A1* 2/2004 Lappe et al. .............. 435/6
2004/0106114 A1* 6/2004 Kocher .................... 435/6
2004/0166583 A1* 8/2004 De Gaulle et al. ........ 436/149
2005/0184153 A1* 8/2005 Auchinleck ............. 235/385

OTHER PUBLICATIONS

"Federal Drug Custody and Control Form", Laboratory Copy, Lab Copy, 7 pages.
"Frequently Asked Questions", eScreen Drug Testing System, 1 page.
Letter to Ms. Misty West from eScreen, dated Oct. 1, 2001, 1 page.

* cited by examiner

FIG. 1

IDENTIFICATION METHOD AND APPARATUS

CROSS-REFERENCE TO RELATED APPLICATIONS

This application is a U.S. NonProvisional patent application and claims priority to and the benefit of U.S. Application No. 60/423,955, filed Nov. 4, 2002, hereby incorporated.

BACKGROUND

Generally, an aspect of the inventive technology relates to an identification system for accurately and adequately identifying events or materials. Another aspect relates generally to new methods and apparatus relative to more efficient generation of a custody and control form. Specifically, at least one embodiment of the inventive technology focuses on an encrypted, character-based identification information item that is based on facts related to the event, substance, or object that it is intended to uniquely represent and thereby identify. At least one embodiment of the custody and control form aspect of the apparatus focuses on computerized generation of a specimen specific custody and control form through electronic population of at least a majority of the specimen specific custody and control form upon input of a certain number of characters. Yet another aspect of the inventive technology generally relates to an efficiency-enhanced process for assigning to individuals that are to undergo an off-site specialized procedure (e.g., a sample collection for drug testing by, e.g., a toxicology lab, or a sample collected for clinical testing by a clinical lab) the geographically most proximate site capable of performing this procedure. In a preferred embodiment, this novel method utilizes commercially available mapping software.

Substance abuse by employees is and has been a problem for employers for many years. It compromises employee productivity, lowers workplace morale, impairs job performance, and decreases job-site safety, among having other effects, resulting in perhaps hundreds of millions of dollars of losses for employers worldwide. Even employees who are not under the influence of a drug at work, but perhaps use only during weekends or after work, may not be as productive, alert, safe or effective employees as they would be otherwise. The desire to abate the ill-effects of drug use by certain groups of people (as but a few examples, employees, athletes, students and inmates) has been known for some time. Indeed, employers and others have responded to this problem with substance abuse testing of employees in order to abate the ill-effects of substance abuse. Such efforts have become key in assuring or at least improving compliance by individuals in a workplace or other setting with relevant substance abuse policies, laws or regulations to which the individuals, employees and/or workplace are subjected.

Generally, such compliance verification effort involves collection of a specimen (e.g., urine, blood, hair, tissue, oral fluid, as but a few examples) which, when tested properly, may indicate prior use by the individual tested of the target substance(s) (i.e., that substance, such as cocaine, e.g., whose use would violate an applicable policy, law or regulation). This collection occurs at a collection site, which, although typically a specialized facility that is physically separate from the individual's designated location (e.g., a factory, school, prison, or office, as but a few examples), may be located at the individual's designated location (on-site). Again, it should be understood that it is not only employers that might sponsor testing of individuals—indeed, any organization or entity, generally known as a sponsoring entity, might initiate testing of individuals affiliated with it for prior substance abuse or drug testing. An additional step involves analytical specimen testing in, e.g., a laboratory or, sometimes, onsite (at the collection site such as the workplace, e.g.). This testing typically involves the use of specially adapted analytical equipment; the test result may be positive or negative, or where an onsite testing kit is used, negative or non-negative. Often, but not always, in order to assure that a positive or non-negative result indicates use of a drug or substance in violation of a law, regulation or policy, a medical review officer may conduct a review or investigation (again, to assure that the use is not a legal, legitimate or approved use). Such medical review is often used in the case where a positive result is found, but where a positive result is found for a prospective new employee (before employment is commenced or any agreement to do so is met), the medical review process may be foregone and the prospective new hire simply not hired. Similarly, where a test kit is used (e.g., an on-site test kit) for a prospective new hire before a more reliable laboratory test is performed, a test kit result of non-negative may cause the sponsoring entity (the employer, e.g.) to simply forego the laboratory test and simply not hire the prospective new hire. Relevant in this regard is the Thct that one of the purposes of the medical review process is to improve or assure the integrity of the testing. Another step taken to assure the integrity of the test result and specifically to improve the likelihood that a test or testing process will withstand a legal challenge by, e.g., a tested individual whose employment has been terminated due to a positive result, is the use of a custody and control forms (also referred to as a chain of custody form).

However, the use of the custody and control form is not limited to drug testing, as a sample or specimen collection may be for clinical testing. Clinical testing includes testing and analysis of any substance collected (e.g., biopsies, tissue, blood, bodily fluids) for disease, abnormality, levels of a constituent (e.g., cholesterol); precursors to disease, or, indeed for any indication that remedial or treatment measures may be appropriate and benefit the health of the donor. Specific examples of clinical testing include testing for cancer, pap smears, testing for antibody or antigen presence, testing of blood) and, generally, testing of any bodily substance for any indication of less than optimal health.

The custody and control form plays an important role in substance use and clinical testing. It is valuable at least in that, when properly completed or adequately specimen specific, it can be evidence that the specimen (also known as a sample) was not tampered with in any manner during that period of time from collection of the sample from the donor (the tested individual) to testing of the sample. Typically, one may find indicated on a completed or adequately specimen specific custody and control form the following specimen specific custody and control form information items: an account information item (e.g., a number) for billing purposes; collection site information, including perhaps the site location and the identity of the collecting individual; the identity of the medical review officer (if applicable); the identity of the laboratory analyzing (or testing) the collected sample for indication of use of the target substance(s) by the donor; a specimen identification number (generally a required item); the donor's signature, and/or the collecting individual's signature or initials. It should be understood that an item of information can be a collection of data, facts, or characters, a set of data, facts or characters, in addition to merely one character). Often, the collection site (whether it be a specialized collection site or an on-site collection site that is located at, e.g., the employee's office) will obtain on its own the custody and control form (in addition to items or materials necessary for the actual sample collection, such as a cup for urine collection). The collection site may instead have received the custody and control form and/or the sample collection equipment from the laboratory, from the donor, or from the sponsoring entity. Regardless of how or from whom the custody and control form is obtained, conventional methods of placing specimen specific custody and control form information items onto a blank or only partially completed or partially specimen specific custody and control form involve manual, time consuming and labor intensive, manual "character-by-character" entry by the collection site and perhaps also the lab, MRO and third party administrator, including handwriting onto a paper copy, typing using a typewriter onto a paper copy, or typing using a computer keyboard into appropriate fields or spaces of an on-screen computer image. It is important to understand the these problems, although presented herein as being limited to custody and control forms, are found wherever manual, character-by-character data entry is required, including in the context of authorization forms. Regardless of the specific application in which the problem is found, there has indeed been a long-felt but unmet need to eliminate or at least reduce the extent of such entry.

Such manual character-by-character entry is time-consuming, inefficient, and prone to error. Further, when such data is entered character-by-character at the collection site (or indeed at any other site that specializes in pursuits and tasks other than such data entry), the need to effect such entry typically interrupts the task of at least one employee engaged in another pursuit. Such interruption and devotion of time and effort to such data entry compromises efficiency of that particular site (e.g., that collection site). Obviating the necessity of such "de-centralized" data entry would enhance efficiency of that particular site and of the overall system, perhaps reducing labor and material costs to testing service providers (including third party administrators that administrate and/or manage one or more aspects of the testing).

Were the data entry centralized at some point so that such task were an assigned and designated task to be performed by a trained employee who would expectedly devote blocks of uninterrupted time to accomplish such data entry, the aforementioned interruption associated with character-by-character data entry could be avoided or minimized and collection site (or other site or entity) efficiency would result. Such centralization could be further enhanced by, e.g., provision of software that enhances the efficiency of data entry.

Provision of a method(s) that avoids the need of any test related service provider (e.g., a specialized collection site, a third party administrator, an analytical testing laboratory, a medical review officer) to perform at least the majority of character-by-character data entry onto the custody and control form at that site can enable cost savings and free up time to better provide their service. Additional savings may be realized through exploiting new opportunities to rely on databases that are already in existence. Such databases include databases that have any data or information relative to specimen specific custody and control form information items (employee social security numbers, e.g.). Such reliance would preclude the need by any entities involved in providing the testing service to enter such data, thereby saving costs for those involved in the testing effort, in addition to avoiding another opportunity for errors to occur during a data entry event.

The custody and control form may have specimen specific information items added to it at any time during the testing process, whether at the client site (e.g., the employer office or workplace), or at the collection site, as but two examples. This information typically may include donor identifying information (e.g., name of the donor, and/or social security number of the donor) the collecting individual's name and/or signature and/or initials, the collection site, an analytical laboratory that may test a sample or specimen, the date of sample collection, any medical review officer that may be used in the process, the sponsoring entity, any third party administrator of any facet of the testing process, and perhaps also information relative to authenticity of the sample (e.g., for a urine test, a temperature strip reflecting the temperature indicated by the filled cup). At any time during the process (although this typically occurs shortly after the collection event), several individuals or entities may be given copies of a custody and control form that includes at least some of the specimen specific information items (often the custody and control form will be sent or shipped with the collected sample to a testing laboratory, but it may merely be made available online). Such a form may be referred to as an at least partially specimen specific custody and control form. An adequately specimen specific custody and control form indicates that that custody and control form includes at least those specific information items necessary to meet legal, policy or other requirements applicable to custody and control forms. Which items are necessary to render a custody and control form adequately specimen specific may depend not only on proper legal jurisdiction, but also at which point in the testing process the custody and control form is. For example, a custody and control form that includes certain specimen specific information items, but has no information relative to a laboratory's date of receipt and individual receiver of the specimen, may be an adequately specimen specific custody and control form at the time of collection but may not be adequately specimen specific after the time of receipt of the transported sample by a testing laboratory. For a custody and control form to be adequately specimen specific after the time of receipt of the shipped sample by a testing laboratory it may indeed need to have information relative to the date of receipt of the sample by the laboratory, the identity of the individual receiving the sample, and/or initials, signature or name of the individual receiving or testing the sample.

Additionally, the client, collection site or laboratory may create an electronic version of the at least partially specimen specific custody and control form (whether after they add additional information items to it or not) by electronically scanning it, and taking other necessary measures to render this scanned version available online. At any point in the process (including after some specific information items are character-by-character entered onto the custody and control form, and indeed, even before any of the information items are indicated in some manner on the form) it may be desired to print an electronically saved copy of the custody and control form so that specific information items can be written or typed onto the paper copy, and/or so that a tangible custody and control form can be sent along with the sample to a certain destination (e.g., a testing laboratory). Using conventional methods, unless the saved copy has all or most all of the information items indicated on it in some manner so that it is an adequately specimen specific custody and control form at that point in the testing process, the remaining information items may need to be manually, character-by-character entered in some manner onto either a paper copy of the incomplete custody and control form, or onto an electronic version of the incomplete custody and control form (typically through use of a computer keyboard and any necessary word processing software) in order to create an adequately specimen specific custody and control form. This is, of course, a time consuming process, particularly where the saved form is initially blank.

In addition to the aforementioned disadvantages of the manual character-by-character data entry of convention methods of generating an at least partially specimen specific custody and control form, when electronic scanning is used, the later printing of at least partially completed custody and control forms is, given the imperfect quality of the electronic scanning process, of lower quality than the paper custody and control form that was originally scanned. Further, the scanning process of course, requires an expensive electronic scanner and significant amounts of computer memory, not to mention the frequent occurrence of scanning errors (a "r" next to a "n" on a document is often read by a scanner as a "m").

Further, using conventional methods, different parties involved in the testing process (e.g., the MRO, the collection site, the laboratory) perform duplicate re-entry steps in that the same data (e.g., specimen donor identification information item, time of collection, etc.) is often entered by each party at least once, and maybe each time an at least adequately specimen specific custody and control form is desired. Thus, the collection date may be entered at least three times (once by the collection site, once by the laboratory, and once by the MRO); such duplicative significantly compromises efficiency of the overall process, increases the opportunity for errant data entry, and generally increases costs of the process.

To further assure the integrity of the testing process (whether needed for the custody and control form to be adequately specimen specific or not), a tangible custody and control form (e.g., paper) may incorporate a signable, flexible, transferable unopened sample container assurance element, such as an adhesive paper strip, that is removable from the custody and control form and transferable around the seal formed by a closure apparatus (e.g., a lid) of the container holding the collected sample. Typically, that signable, flexible, transferable unopened sample container assurance element (which has indicated on it a specimen identification information item), would first be attached by the collector and through adherence to a closed container that contains the collected sample. It would then be signed by the donor. Ideally, the application of the signable, flexible, transferable unopened sample container assurance element would occur as soon as possible after the installation of the sample into a container and the immediately subsequent closure of that container. Signing of the signable, flexible, transferable unopened sample container assurance element would ideally occur immediately after its application to the container seal, and within sight of the donor, thereby enhancing or assuring sample authenticity. Opening of the sealed sample vial or container would typically occur at an analytical testing laboratory immediately before testing of the sample.

Often, a third party administrator will be engaged by the sponsoring entity (e.g., an employer), the collection site (if different from the employer), the analytical testing laboratory, and/or the medical review officer(s) to manage the administrative aspects of any aspect of the testing. Aspects of the testing that may be managed by the third party administrator include specifics relative to specimen collection, specimen analytical testing, and medical review, payment collection and distribution, quoting, and event scheduling (such as sample collection scheduling) or coordinating, perhaps among others.

Another problem inhering in conventional drug and clinical testing administrative processes is loss, whether through administrative, handling or other type of error, of crucial data (as but two examples, the specimen identification number, and the testing result), forms (such as the at least partially specimen specific custody and control form), or materials (such as the collected sample). What might contribute to or compound the problem is lack of recognition of the problem in a timely fashion, causing delay in the testing process, finger-pointing as to who is responsible, losses in time and effort by the testing entities, any third party administrator, the employer and the employee, a need to re-perform some or all of the testing processes, and a general negative reflection on the competence of the testing entities and any third party administrator that may exist. At times, using a conventional drug or clinical testing system, lack of timely recognition of any errors that seem to inevitably occur in the testing process exacerbates the problem caused by the error itself. Such lack of timely recognition is in greatest part attributable to the absence of any means for either prompting or informing parties involved in the drug or clinical testing process that an event that requires action on someone's part (even if that action is merely receiving a collected sample, e.g.) has occurred, or merely providing to those parties access to information relative to the occurrence of a first event, this first event a necessary prelude to a second event.

Yet another area for improvement in the conventional manner of testing (for use of controlled substances, and clinical testing) relates to how specimens are identified and tracked. Conventional methods use specimen identification numbers that, other than perhaps being numerically correlated in some manner with an immediately preceding sample collection or test assignment, for example, are entirely arbitrary in that they are not based on facts related to the specimen collection (e.g., facts relative to the time of collection and the person from whom the sample is collected). For these reasons, they may also be said to be factually disconnected from specifics of the collected sample. As such, they constitute an additional piece of data, require an additional database, and require capability (through software, perhaps), to accurately correlate this arbitrary, factually disconnected sample identification number with a donor name and sample collection time so that upon input of the arbitrary, factually disconnected sample identification number, information sufficient to adequately identify the sample or specimen (information relative to, e.g., the donor's identity and the time of collection of the sample) is revealed to an inquiring individual. Thus, their use introduces an additional opportunity for error into the system, in addition to requiring additional labor and computer equipment relative to retrieving data necessary to adequately specify or identify the specimen.

A system or method that eliminates the need for any of the aforementioned requirements attendant use of conventional specimen identification numbers would save cost in computer equipment and labor, with the ancillary benefit of reducing the risk of error in the system. Further, given that there are currently no measures to assure that different entities that assign specimen or sample identification numbers (as but two examples, different testing laboratories or different collection sites) are using the same sample identification number for a different sample (whether that sample be from a different person or given at a different time by the same person), the current system is not without risk of some error stemming from the use of the same sample identification number for a different sample.

A further disadvantage attendant conventional methods is observed during any facet of service administration or management (each of which included fee or cost quoting for, e.g., drug or clinical testing of a company's employees) that involves the determination of whether a sufficient number of a necessary facility (e.g., specialized sample collection sites) are proximate a certain area. Indeed, a client such as a company that desires to engage a third party administrator to administer drug or clinical testing of affiliated individuals (e.g., employees) may be located (or may have a related facility such as a branch or satellite office, or a factory, e.g., so located) in an area in which there is an insufficient number of necessary facilities to accommodate the company's needs in that area. For example, a company having its employees located at a company factory in Coeur D'Alene, Idaho might request testing services but, during a potential third party administrator's generation of a quote for testing that company's employees working at the Coeur D'Alene factory, the third party administrator might learn that in fact there are no collection sites in Couer D'Alene (or that the number of sites is insufficient to handle that factory's testing needs). Using conventional techniques, measures may be taken by the third party administrator to determine whether any sites are in a sufficiently close distance to the company's factory. These measures typically involve manual use of a table of collection site locations and a map to estimate distances and drive times. Of course, such is inefficient, interruptive and imprecise.

SUMMARY OF THE INVENTION

The present invention includes a variety of aspects which may be selected in different combinations based upon the particular application or needs to be addressed. In one basic form, the invention discloses a novel generation of a custody and control form that finds application in drug use or clinical testing, among other fields. At least one embodiment of another aspect of the inventive technology discloses methods and apparatus relative to an encrypted, character-based identifier usable to adequately identify an event (a purchase, e.g.), an object (a product purchased, e.g.) or substance (a specimen collected from an individual for drug or clinical testing); in a preferred embodiment, this identifier is based on a time and entity associated with the event, object or substance to be identified. Yet another aspect of the invention relates to a novel manner of managing those sponsoring entities who desire specialized services provided by a specialized facility at a location other than an office or factory where individuals to undergo the specialized service are located (e.g., located offsite). Specifically, at least one embodiment of this aspect of the invention involves the novel use of mapping or geographical software in conjunction with information as to the location of these specialized facilities so as to accommodate such off-site needs and prepare an proper quote for provision of such services. Naturally, as a result of these several different and potentially independent aspects of the invention, the objects of the invention are quire varied.

A key application of the present inventive technology is drug testing (a term including drug use testing, illegal drug use testing, illicit drug use testing, drug abuse testing, substance abuse testing, controlled substance use or abuse testing, and prohibited substance use or abuse testing). However, as to the custody and control form generation aspects of the invention, other applications include wherever a custody and control form is used (including drug testing, criminal investigations and police evidentiary work, in addition to clinical testing, of course). As to that aspect of the inventive technology related to the novel identification methods and apparatus, applications include not only specimen identification (e.g., a specimen collected from an individual for drug or clinical testing purposes, or a specimen of evidence), but also event (a purchase, e.g.) identification, object (a product purchased, e.g., and also including specimens) identification, or substance (as but a few examples: blood for analytical testing, dirt for analytical testing, or a specimen collected from an individual for drug or clinical testing) identification.

One of the broad objects of at least one embodiment of the invention is preclusion of manual, character-by-character data entry of these third number of characters by anyone involved in provision of the testing process One of the broad objects of at least one embodiment of the invention is preclusion of the efficiency compromising interruption of workflow attendant on-site data entry of conventional methods.

One of the broad objects of at least one embodiment of the invention is a general improvement in efficiency of the overall testing process.

One of the broad objects of at least one embodiment of the invention is an improvement in the accuracy of sample or specimen identification information items and the reduction or elimination of errors stemming from the inadvertent use of the same specimen identification information items for two different specimens (or, indeed the use of the same element identification information item for two different elements).

One of the broad objects of at least one embodiment of the invention is the preclusion of any need by different entities that assign specimen identification information items to cross-check among themselves to assure that no identical specimen identification information item is used for two different specimens.

One of the broad objects of at least one embodiment of the invention is provision of the opportunity to rely on pre-existing databases in generating a specimen specific custody and control form, thereby reducing the need for manual, character-by-character data entry.

One of the broad objects of at least one embodiment of the invention is the reduction or elimination of duplicate data entry in the entire process, whether that duplicate data entry be by one party (e.g., the laboratory entering the time of collection more than once) or several parties (e.g., the collection site and the laboratory entering the time of collection once each).

One of the broad objects of at least one embodiment of the invention is the abatement or elimination of the problem relative to delayed recognition of the failure of an event to occur (e.g., the receipt of a test result, or the receipt by a laboratory of a collected sample).

One of the broad objects of at least one embodiment of the invention is the efficient gathering of information relative to the location of off-site specialized facilities, and specifically relative to a most proximate offsite specialized facility, for use by, e.g., an administrator of the service so that a proper cost quote for this service can be given to a service consumer, and so that location information relative to the nearest specialized facility can be provided to an individual to whom the service specifically relates.

Naturally, further objects of various embodiments of the inventive technology are disclosed throughout other areas of the specification and claims.

BRIEF DESCRIPTION OF DRAWINGS AND EXHIBITS

Exhibit A includes copies of possible website screens that are usable by a computer user and facilitate use of at least one embodiment of the inventive process.

Exhibit B includes copies of custody and control forms that may relate to at least one embodiment of the invention.

DESCRIPTION OF THE PREFERRED EMBODIMENTS

Figure 1:
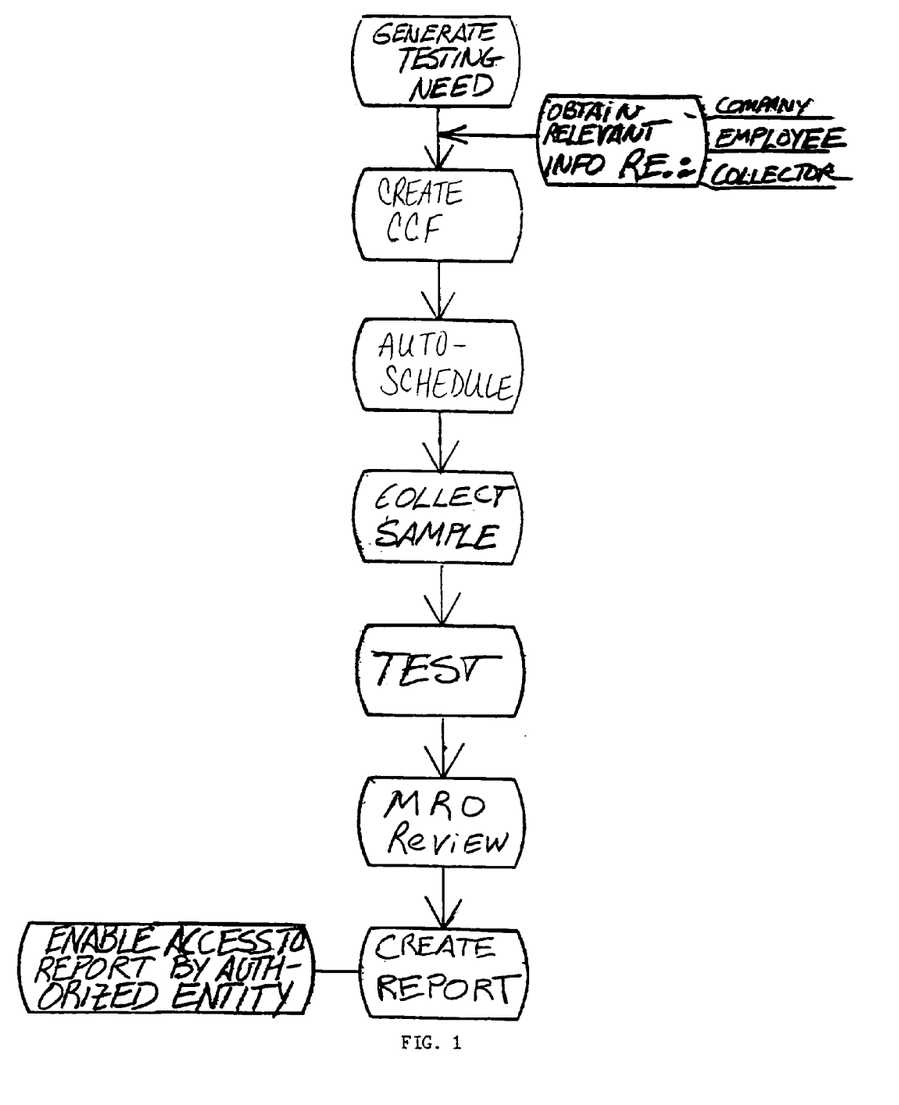
FIG. 1 shows a graphic presentation of steps of at least one embodiment of the inventive process, wherein at least one of the steps may be performed using software and/or on an electronic communication medium such as the internet.

As mentioned earlier, the present invention includes a variety of aspects, which may be combined in different ways. The following descriptions are provided to list elements and describe some of the embodiments of the present invention. These elements are listed with initial embodiments, however it should be understood that they may be combined in any manner and in any number to create additional embodiments. The variously described examples and preferred embodiments should not be construed to limit the present invention to only the explicitly described systems, techniques, and applications. Further, this description should further be understood to support and encompass descriptions and claims of all the various embodiments, systems, techniques, methods, devices, and applications with any number of the disclosed elements, with each element alone, and also with any and all various permutations and combinations of all elements in this or any subsequent application.

At least one embodiment of the inventive technology is a method generating an at least partially specimen specific custody and control form having a first number of characters of specimen specific custody and control form information items by inputting data having a second number of characters, actuating generation of the form, and electronically populating an incomplete custody and control form with a third number of characters of specimen specific custody and control form information items, where the second number is less than 25%, 20%, 10%, 5%, 3%, or 1% of the first number, and where the third number is not greater than the first number. Such population may be accomplished via computer and by anyone involved in the testing process and having sufficient specific information to at least partially specify a collected sample (either existing or expected) to which the custody and control form is to be correlated. It is, at least in large part, the step of electronically populating with the third number of characters of specimen specific custody and control form information items, that effects such a dramatic improvement in process efficiency (including speed), specifically through (a) preclusion of manual, character-by-character data entry of these third number of characters by anyone involved in provision of the testing process; and/or (b) preclusion of the efficiency compromising interruption of workflow attendant on-site data entry of conventional methods. This improvement in efficiency is a significant advance over the prior art; it is not merely a gradual slope of improvement.

Populating refers to a fast (e.g., less than 5 seconds, and including instantaneous) provision of the indicated data to the indicated form, and perhaps incorporation therein by, e.g., placement into the appropriate spaces on the form. It does not involve character-by-character data entry performed by a person, nor does it include bringing up an electronically scanned copy.

Inputting data may be accomplished in any manner, including, e.g., manual, character-by-character entry, entry using voice recognition software, and scanning; in a preferred embodiment, the data input is a second number of characters of specimen specific custody and control form information items and, where such is the case, the third number may be less than the first number (because the input data itself, in such a case perhaps a specimen specific custody and control form information item, may appear on the form). In such a case, the second number plus the third number may be equal to the first number. The input data (a broad term to include anything that is character-based, or renderable in character form), instead of being a specimen specific custody and control form information item, may be any character-based input that is not specimen specific, e.g., an access code that then enables actuation of the form generation (or perhaps automatically actuates form generation). Data inputting may be accomplished through inputting data into a data receipt element—which may be a computer or computer component, e.g., that is adapted to receive said data (perhaps by having a keyboard and other componentry necessary for data input).

Actuating generation of a form may include merely hitting a certain button (e.g., a computer mouse button or an enter button), or it may occur automatically after the aforementioned data input step is accomplished. Any of these, including that related to user actuation and automatic actuation, is a type of form generation actuation element. In a preferred embodiment, the method is a method of generating an at least partially specimen specific drug testing custody and control form, but the method may be applied in any context involving the use of custody and control forms (e.g., a clinical testing custody and control form); similarly, the preferred apparatus embodiment is an at least partially specimen specific drug testing custody and control form generation apparatus, but may be broadened to cover other applications (such as clinical testing or evidence testing).

In at least one embodiment of the inventive technology, the step of electronically populating an incomplete custody and control form with a third number of characters of specimen specific custody and control form information items comprises the step of retrieving characters from at least one database; it may be accomplished by an electronic, form population element, which may be any type of computer componentry that can accomplish said population, including, perhaps, software that enables retrieval of data or characters from databases. Such retrieved characters may have been input into the database offsite (e.g., at a site other than the site where the step of actuating generation of the form is performed). Such database may be a client-prepared (e.g., a sponsoring entity-prepared) database of, e.g., employee specific data such as employee number or social security number.

The at least partially specimen specific custody and control form is a custody and control form that is not blank and has at least one specimen specific information item indicated on it. It may find use with the collected sample, perhaps when that partially specimen specific form is made adequately specimen specific. Information that might be found on such an adequately specimen specific custody and control form typically includes a sample identification information item (e.g., a number, an alphanumeric identifier, or generally, a character-based identifier) and may include one or more of the following specimen specific custody and control form information items: client identification information item (e.g., employer identifier), collection site identification information item, analytical laboratory identification information item, medical review officer identification information item, client account identification information item, and third party administrator, as but a few examples. An adequately specimen specific custody and control form may also include specific information items that are supplemental to those specific information items that render the form adequately specimen specific.

As mentioned, generation of an at least partially specimen specific custody and control form may involve electronic population of an incomplete form (e.g., one that does not have every blank space completed) with one or more of any of these specimen specific custody and control form information items. The term incomplete custody and control form is different from an at least partially specimen specific custody and control form in that the term incomplete form includes blank forms, partially specimen specific forms, and even some adequately specimen specific forms (but, again, excludes forms having every possible piece of information that could be added) while the term at least partially specimen specific excludes blank forms but includes adequately specimen specific forms and even entirely completed forms. It may be required that, for a custody and control form to be adequately specimen specific, it must be signed or initialed by a certain individual(s), e.g., the collector and/or the donor. Thus, the term adequately specimen specific custody and control form includes those information items (e.g., possibly the signature or the initials of the collector and/or the donor) whose presence on the custody and control form is either advisable or required under relevant law, policy, guidelines, or accepted general practice.

In at least one embodiment of the inventive technology, a specimen (or sample) identification information item (or other specimen specific custody and control form information item) regardless of how or by whom generated, is provided to or obtained by the collection site (perhaps by the donor, laboratory or the client such as an employer of the donor, e.g.) and, upon input of this information item, is usable to populate online a custody and control form (often a blank form) so that it becomes an at least partially specimen specific custody and control form. However, the inventive technology also covers populating upon entry of other data.

If an at least partially specimen specific custody and control form is not adequately specimen specific, then measures are typically taken by the collection site (e.g., by the collector) or at other points in the testing process to render such partially specimen specific custody and control form adequately specimen specific. Such measures may include, e.g., signing or initialing by the collector and/or lab technician, and/or obtaining the donor's signature (which may be done using a writing implement or electronically), or adding any other remaining specimen specific custody and control information items.

Exhibit B shows a sample custody and control form. The custody and control form may mirror the federally mandated form used in collections for those employees under the regulations of the Department of Transportation (DOT) and may be used for DOT-mandated tests and testing. This form may also be used for Non-DOT purposes and may be identified as a non-regulated collection in those situations.

All methods of signing, including electronic signing are usable to create any signatures that may be necessary to render a custody and control form adequately specimen specific. Electronic signatures may reduce the risk of illegibility of the custody and control form and loss of the form.

The process may also allow the collector to store the electronic image of the custody and control form for future reference and to enable "e-mailing" or other electronic transmission of the appropriate copy of the custody and control form to the Medical Review Officer or Medical Doctor's organization, to the Laboratory performing the test, or to the entity authorizing the collection, as but a few examples. Indeed, certain forms and/or pieces of information may be rendered communicable to or with only certain entities. For example, it may not be appropriate to provide to the laboratory the name of the donor.

At least one embodiment of the invention discloses an electronically (such as internet) based process that may improve the reliability, validity and/or integrity of the Custody and control form. At least one embodiment of the invention is the electronic or computer based provision of a database of lab, employee, collection site and collectors that is usable to create a specific chain of custody which may be electronically signable by the donor and the collector and electronically communicable (via transmission, e.g.) to appropriate entities (e.g., the company employing the donor, and the medical review officer whose function it may be to review positive test results, as but two examples). The collector may, using the inventive process, have the opportunity or ability to create a Custody and control form usable in the collection process to accompany the specimen being shipped to the laboratory.

Once signed, the online custody and control form may be secured (as read-only, as but one example) such that no alterations to the form will be allowed, thereby enhancing security. The original signed copy of the custody and control form may be provided to the donor as their copy of the event. A bar code may be attached to (electronically, e.g.) or in some way made to be uniquely associated with a specific custody and control form, this bar code perhaps including on it the specimen identification information item (which of course may be encrypted). At least one embodiment of the inventive process may enable printing of a copy for the Medical Review Officer or Medical Doctor's organization or printing of a copy for the entity authorizing the collection.

According to at least one embodiment of the invention, once a result of the test is complete, that result can be accessed (online, e.g.), but perhaps only by authorized entities. The online result may include the donor's first and last name, identification number, authorizing entity, specimen identification information item, reason for the test, date the collection was performed, the location of the collection, date any Medical Review Officer received the custody and control form, and the result of the test (as this is not an exhaustive list, these are but a few examples).

In addition to the provision of online individual test results to the authorizing entity, statistical reports for time periods entered by the user that reflect positive rates, quantities of reasons for the tests, and quantities of each of the types of results may also be available online. Using the inventive process, a user may be able to view a model substance abuse testing policy (including forms) and procedure manual and past invoices. Viewing and comprehension of the policy may be facilitated by computer based links that are usable to access definitions and other relevant information usable to clarify certain policy text. A user of at least one embodiment of the inventive technology may be able to create turnaround time studies as well as view their random selections or current performance to the appropriate percentage. In addition, a user may be able to add donors and delete donors from an active list used for random testing, and generate a list of those donors who have been random tested as well as those who still need to be tested.

At least one embodiment of the invention may also disclose the generation and/or provision of the MIS report (a statistical report that may be created for and/or made available for the Department of Transportation) online or via some other electronic communicative medium. The report may include, inter alia, information regarding why a certain test(s) was performed (e.g., reasonable cause, random, pre-employment, periodic testing, return to duty, follow up, among possible other reasons), and the result classification of the test (e.g., positive, negative, refusal to test, reversal of positive to negative).

At least one embodiment of the invention may include an internet-based process that includes what may be termed a results query functionality. More specifically, this feature may enable an authorized entity to specify certain parameters in order to generate a report that summarizes factual date regarding testing and results according to those parameters. For example, a client may want to know the number of positive results for all donors employed by a certain company tested in a certain geographical area during calendar year 2000. The results query feature could be used to generate such information in the form of an MIS report, e.g.

At least one embodiment of the invention may include an internet-based process that includes what may be termed a results query functionality. More specifically, this feature may enable an authorized entity to specify certain parameters in order to generate a report That summarizes factual data regarding testing and results according to those parameters. For example, a client may want to know the number of positive results for all donors employed by a certain company tested in a certain geographical area during calendar year 2000. The results query feature could be used to generate such information in the form of an MIS report, e.g.

At least one embodiment of the inventive technology focuses on a novel specimen (or sample) identification method and apparatus. Given that one sample will be collected from a donor at one time, a specimen identification information item that includes information items that are unique to that time (as used herein, time refers to either time of day and date, or simply date, or even simply year) and unique to that donor will be sufficient to adequately identify the sample from all other samples, without requiring any cross-checking against other such specimen identification information items (such cross-checking is a measure that may be taken to assure that different entities that assign specification identification information items do not use identical specimen identification numbers for different specimens). Use of such a novel sample identification information item will also eliminate that opportunity for the generation of errors attendant the conventional arbitrary specimen identification number. Relatedly, such use may also reduce data entry needs, as the novel specimen identification information item may be at least partially based on information that may already be input into the system (time of collection and donor identification information item). Also, because the novel specimen identification information item may be based on information that may already be input into the system, its use may eliminate the extra effort and costs (associated perhaps with referring to a surplus database having correlation information) to identify which specimen the arbitrary number correlates with.

In a preferred embodiment, the specimen identification method incorporates in some manner information usable to identify the time the sample was collected (sample collection time information item, which may be a date or a time of day and date), and the individual from which the sample was collected (donor identification information item). The method may comprise identifying a specimen donor with a specimen donor identification information item (a social security number, a driver's license number (perhaps with state code specification), as but two examples); adequately specifying a specimen related event identifier (e.g., a specimen collection event identifier such as a time of collection); associating the specimen donor identification information item with the specimen related event identifier; and, in response to this step (e.g., by performing this step), generating a unique specimen identification information item. The specimen related event identifier may be a time, a term that includes (a) merely a date such as a specimen collection date, (b) a date and an adequately specific time of day of specimen collection; and also (comprises) a year, perhaps that year during which the specimen collection took place. By adequately specific is meant specific enough to adequately identify the event so that, when used in conjunction with a specimen donor identification information item, the resultant information item will be sufficiently reliable to identify as desired. An adequately specific time of day may thus merely be an indication as to AM or PM, or, at the other extreme, may need to be as detailed as 9:48 PM, 52 seconds, with perhaps an indication as to fractions of a second, including any levels of specificity therebetween.

The unique specimen identification information item may be a character-based specimen identification information item and may be substantially contiguous, a characterization that applies even where there may be spaces between characters of the specimen identification information item but the specimen identification information item is still contained within a space so that it may be viewed in its entirety without having to search other parts of the form or label on which it may be found. Thus, the following six specimen identification information items (also types of specimen identifiers, element identification information items, and element identifiers) would be substantially contiguous specimen identification information items or identifiers (as but a few examples):

12130321759*D523*

121403    217$975*U3*

121 703

217597 &*K23*

1212032135 97*NB23*

12 09 03 217 59 7*X23*

1 21 20 221*K593*    523

In a preferred embodiment of the inventive technology, certain measures are taken to encrypt the donor identification information item (e.g., social security number, or other character-based identifier), or at the least, make this information not immediately discernible, for privacy and/or other reasons, so that the specimen identification item is an encrypted specimen identification information item (or more generally, a not immediately discernable specimen identification information item). Wherever the donor identification information item is encrypted or made not immediately discernable (or, for that matter, whenever any component of the specimen identification information item is encrypted or made not immediately discernable), the specimen identification information item is an encrypted specimen identification information item (or a not immediately discernable specimen identification information item).

Upon rendering a specimen donor identification item (or indeed the specimen identification information item or any component thereof, including the specimen related event identifier) not immediately discernable, or upon encrypting this information item or identifier, a discernment process (or decryption algorithm) specificity information item may be associated with this not immediately discernable (or encrypted) information item or identifier. The discernment process (or decryption) specificity information item may be simply that step or steps necessary to render the not immediately discernable information item or identifier immediately discernable, or that step or steps necessary to decrypt the encrypted information item or identifier. Such steps may be, e.g., the reverse of the steps employed to render the information item or identifier not immediately discernable, or the reverse of the steps employed to encrypt the information item or identifier. As but one of perhaps countless examples of such step(s) to render immediately discernable or decrypt is (a) subtract 3 from each single digit number that is in the not immediately discernable or encrypted information item or identifier; and (b) change all 7's to 4's of the numbers resulting from the performance of step (a). Other steps may include rearranging characters so that not all characters are in that location that would make the information item or identifier immediately discernable. These steps may be performed by computer, perhaps automatically or after actuation, or in any other manner (as may be the reverse of these steps which were used to render not immediately discernable or encrypt the information item or identifier).

A character-based discernment (or decryption) code (as but one example, a number) may be associated with the discernment process (or decryption algorithm) specificity information item, this code thereby representing the discernment process (or decryption algorithm) specificity information item. Through this association may be created perhaps a code representation information item. The code representation information item may be database or other set of correlated information that is usable to determine a process to render immediately discernable a not immediately discernable specimen identification information item, or an algorithm to decrypt an encrypted specimen identification information item, when the associated, correlated or representative code is known.

Regardless of whether any component of the (unique) specimen identification information item (a term that includes immediately discernable, not immediately discernable, and encrypted specimen identification information items) is rendered not immediately discernable or encrypted, or whether instead it is the unique specimen identification information item that is rendered not immediately discernable or encrypted first (with any rendering of its component parts not immediately discernable or encrypted merely as a result of this initial effort), the character based code may be associated with the unique specimen identification information item.

Such association may be, e.g., a visual association, as where the code is placed somewhere on the same custody and control form as is the unique specimen identification information item so as to facilitate rendering discernable or decryption of the specimen identification information item (by perhaps only authorized persons or entities). It may be even more visually associated than a mere placement on the same form if it is established as part of the specimen identification information item. Similarly, the step of generating a unique specimen identification information item may comprise the step of generating a specimen identification information item that itself comprises the aforementioned code.

Of course, the code would facilitate rendering immediately discernable or decrypting a specimen identification information item only in the case where the process or algorithm usable to render immediately discernable or decrypt the specimen identification information item is known to an individual or entity (or made accessible to their computer, e.g., whether the user of the computer knows the process or algorithm or not). Thus, to protect the privacy of, e.g., the individual tested, access to the code representation information item may be limited to only authorized individuals or entities. Such may be accomplished by provision of a code representation access code to only these certain authorized entities (including individuals), or merely by providing the code representation information to authorized entities. Perhaps those who become familiar with the method may learn which character(s) on, e.g., the custody and control form makes up the code, but unless they are in some manner given access to the aforementioned process or algorithm that the code represents, then determining, e.g., who tested positive for cocaine, will be a difficult or impossible process.

An aspect of the inventive technology is a specimen identification apparatus that comprises a specimen donor identification information item associated with a specimen to be identified, and a specimen related event identifier associated with the specimen and appearing with the specimen donor identification information item so as to establish a specimen identifier. By appearing with is meant that the indicated elements are somehow visually correlated, whether side by side in a single-line character-based information item, or merely appearing on the same form or label, as but two examples. Apparatus type limitations relative to a specimen identifier that is not immediately discernable or that is encrypted are roughly corollary (but of course in an apparatus mode) to those limitations described above. Thus, there is herein provided disclosure relative to an inventive specimen identification apparatus.

The inventive technology relative to a navel identification information item is, however) not limited to identification of specimens—only it also covers a more broadly applicable element identification method. In at least one embodiment of a method mode of the inventive technology, an element associated entity is identified with an entity identification information item; a time-related identifier (that identifies a time related in any manner to the element) is adequately specified; the entity identification information item and the time-related identifier are associated, in response to which (e.g., upon whose performance) a unique element identification information item is generated. The element may be a specific event (e.g., the commission of a crime, the performance of a hired service, or a payment, as but three examples), a specific substance (a specimen, which term itself includes any piece of evidence, or collected matter to be analyzed such as blood or soil, as but a few examples), or a specific object (a piece of evidence or a purchased product, as but two examples), while the entity may be, e.g., a person, or organization (including, e.g., a business, a sports team, a non-profit organization, and a government organization) as but a few examples. The time-related identifier may be an event related time, such as the time of occurrence of an event, this event in some manner related to or associated with the element (as but two examples, a gathering of a substance; and the time of purchase of the element, a product). Thus, the element identification method may be a specific event identification method, a specific substance identification method, or a specific object identification method; the element associated entity may be a specific event associated entity, a specific substance associated entity, or a specific object associated entity, and the unique element identification information item may be a unique event identification information item, a unique substance identification information item, or a unique object identification information item. Additionally, the element associated entity may be an element associated person or organization, and the entity identification information item may be a person identification information item or an organization identification information item. The disclosure provided herein, relative to not immediately discernible and encrypted specimen identification information items (both method and apparatus), is applicable also to the element identification method and the element identification apparatus, so as to provide adequate support for both.

A unique event identification information item can itself include a time-related identifier in that the time related identifier may be, e.g., merely a date, while an event identifier may include that date, in addition to information relative to the entity (e.g., a person) associated with the element (the element being, in this case, an event specific not only to that time but also to that person). Thus, in this example, the event for which an adequate identifier is desired may be a purchase by that person on a certain date of, e.g., a vehicle.

At times, during use of a conventional drug or clinical testing system, lack of timely recognition of any errors that seem to inevitably occur in the testing process exacerbates the problem caused by the error itself. Such lack of timely recognition is in greatest part attributable to the absence of any means for either informing parties involved in the drug or clinical testing process that an event (sample collection, e.g.) that requires further action on someone's part (shipping of a collected sample to a lab, e.g.,) has occurred, or merely providing to those parties access to information that would alert them to the occurrence of a first event, this first event a necessary prelude to a second event (e.g., transport of a collected sample). Thus, upon knowing of the first event's occurrence, the party would know to look for the second event. As a simple example, upon being aware of a laboratory's completion of testing of a sample (a first event), a MRO or third party administrator, e.g., would know to look for a test result from that laboratory relative to that sample.

Thus, at least one embodiment of the present inventive technology is directed to precluding that delay in the testing process that is associated with lack of timely recognition of errors. Such preclusion is generally effected by that aspect of the invention directed to the generation of the specimen specific custody and control form that enables certain parties to whom data or material is forthcoming because of the occurrence of an event (e.g., the laboratory may know to look for the collected specimen because a sample has been collected) to look for that data and, if it is not forthcoming in a timely fashion, to take necessary measures to solve or mitigate the problem. Upon its creation, an online custody and control form is usable (whether by prompting, or whether by merely providing stored information that can be accessed) so that an entity (such as a third party administrator, a laboratory, a collection site) can know to look for an expected test-related occurrence. Such pre-scheduling, as where the collection is scheduled in the system before its occurrence, is at least one manner of precluding that delay in the testing process that is associated with lack of timely recognition of errors.

At least one embodiment of the inventive technology may be an internet (or other electronic communicative medium) based process that includes what may be termed autotracking, a feature that may enable communication of certain information, including, but not limited to, information regarding any non-appearance of the donor; a failure of an expected response from a certain entity (such as the laboratory, the collection site or the MRO, as but a few examples), or more generally any information regarding the tracking of the timing and occurrence of events. This information may be communicated or transmitted via email, e.g., to a client or other appropriate entity (e.g., a MRO, collection site, and/or laboratory) that has a legal right to it.

At least one embodiment of the inventive technology is a process that may be accessed and used on the internet to schedule an appointment at a specific location (e.g., a collection site) at which time a donor will provide a blood, urine, oral fluid, hair, or fingernail specimen (or perhaps other type of tissue or fluid specimen) for laboratory or onsite analytical testing. The scheduler may have the capability of selecting a specific donor from a list or entering a donor not on the list, selecting a location from a list where the collection will be performed, entering a date and time for the collection, selecting a reason for the collection, and selecting what form of specimen will be collected. The scheduler may have the capability to print this authorization to a file or remote printer.

Clients such as companies can use at least one embodiment of the inventive technology to scheduling online collection of specimens, and to find out who of their employees has not been tested and schedule an appropriate testing. The collection site also might be able to use the process in order to determine information, such as who has been scheduled at their site. The provision of this information may be facilitated by, e.g., computer based pop-up windows features. Electronic communication such as email might also be used in a confirmatory manner to, inter alia, inform the employee that he or she is scheduled for a test and where and when that test is. Others, such as the collection site, might also be informed of a certain testing date, and information as to not only who is scheduled for testing, but what company that donor is employed by, and/or which company a certain block of donors is employed by.

At least one embodiment of the inventive technology is a process usable on the internet (or perhaps another computer-based or communication medium) by or on behalf of the sample collection site, at the collection location where the scheduled event shall occur, to access a list of those donors who have a pre-scheduled collection or exam appointment at that location. Using the process, the collection site may have the capability of selecting a collector from a list of collectors specific to that location or site, or entering a collector not on the list. The list of collectors may also contain information as to the training certifications of each collector and information as to when that training took place and whether retraining is required. The collector may have the capability to print this authorization to a file or remote printer. The collector may also have the opportunity or ability to access all previous events performed over a specific time period identified by the collector.

At least one embodiment of the inventive technology may involve an integrated online internet process for scheduling a specimen collection or medical exam, and retrieving results and statistical data relative to the collection, testing of the collection, or medical exam.

At least one embodiment of the invention is directed to creation of an authorization form via electronic population) that may include donor specific authorization form information items such as the authorizing entity information (sponsoring entity such as a company with whom an individual to be tested is affiliated), the collection site location information, a donor identification information item, the laboratory at which the specimen is to be tested (perhaps including the account number), and the specific information as it relates to the collection to be performed. The authorization form typically finds use in authorizing the collection site to actually collect the sample or specimen from the individual to be tested. If the sponsoring entity requires an onsite test of the specimen, that information may be in addition to information as to any laboratory that may be used to confirm positive results of the onsite testing device. The scheduler may have the capability to print this authorization to a file or remote printer.

At least one embodiment of the inventive technology addresses a novel method and apparatus relative to generating an at least partially donor specific authorization form having a first number of characters of donor specific authorization form information items. The novel method comprises the steps of inputting data having a second number of characters, wherein the second number is not greater than 25% said first number; actuating generation of the at least partially donor specific authorization form, and electronically populating an incomplete authorization form with a third number of characters of donor specific authorization form information items, where the third number is not greater than said first number. The associated apparatus may be an at least partially donor specific authorization form generation apparatus usable to generate an at least partially donor specific authorization form having a first number of characters of donor specific authorization form information items, this apparatus comprising: a data receipt element that is capable of receiving input data having a second number of characters, where the second number is not greater than 25% said first number, a form generation actuation element (e.g., computer or other electronic componentry) that is adapted to actuate generation of the at least partially donor specific authorization form after the data receipt element receives the second number of characters; and an electronic, form population element (e.g., computer or other electronic componentry) adapted to populate an incomplete authorization form with a third number characters of donor specific authorization form information items, wherein the third number is not greater than said first number. The apparatus may be an at least partially donor specific clinical testing authorization form generation apparatus, or an at least partially donor specific drug testing authorization form generation apparatus At least one embodiment of the inventive technology relates to a novel method for administering services (or a novel administration apparatus) relative to any aspect of the drug or clinical testing process (e.g., sample collection). In at least one embodiment, this novel method involves the use of commercially available mapping software that can in some manner be used in conjunction with information items relative to the location of an off-site facility(ies) so as to enable the efficient provision of information relative to the nearest off-site facility. In a preferred embodiment of the invention, this administration technique comprises the steps of determining a location of each of a plurality of first sites that are each capable of performing a specialized procedure (as but two examples, collection sites capable of collecting a specimen from an individual to be tested for drug use, or for indication of a disease); assessing a need to perform the specialized procedure relative to individuals (e.g., on employees) affiliated with a second site (a factory or school, e.g.); this second site having a location that is different from said location of each of a plurality of first sites; enabling mapping software to access information items relative to said location of each of a plurality of first sites; inputting information relative to said second site location; and automatically determining a location of one of said plurality of first sites that has a smallest second site to first site travel related parameter (e.g., is closest in terms of drive time, or is closest in terms of radial distance from the second site). It should be understood that the term specialize procedure covers any service in which an individual or organization may specialize. The step of enabling mapping software to access information items relative to the location of each of a plurality of first sites may comprise the step of linking information items (e.g., a database) relative to each of a plurality of first site locations (e.g., addresses (perhaps only zip codes) of sample collection sites) to mapping software. The mapping software may be MapPoint or any other such software.

There is at least one unique situation in which the mapping software related aspect of the invention finds particularly helpful application. Specifically, when it is determined that there is an insufficient number of first sites (e.g., collection sites) to meet the needs (e.g., sample collection of employees for drug or other testing) of a second site (a factory or other employee site, or a school or prison, as but a few examples) in the area of the second site (e.g., in the second site's population center such as city, county, zip code, or within a certain radius or drive time of the second site, or in any other geographical limitation, which may or may not be defined by the user), a capability to automatically generate the location of the first site that is nearest the second site would vastly improve administration efficiency as compared with conventional methods. The term insufficient number includes zero, in addition to non-zero numbers in the case where sufficiently proximate first sites (e.g., those having an acceptable second site to first site travel related parameter) are unable to meet expected needs of the second site. Not only might at least a nearest first site be automatically determined, but at least one additional first site (e.g., a second nearest first site) may be automatically determined. As used herein, the travel related parameter may be drive time, distance radius, or any other parameter or index that relates to distance or time of travel in some manner. Indeed, the method may comprise a first site locating constraint which may be a drive time zone constraint (e.g., as may be found in a request for all first sites that are within a ½ hour drive time of a specific second site), or radial distance constraint (e.g., as may be found in a request for all first sites that are within 15 miles of a specific second site).

The novel method for administering services may involve determining a price or cost quote for the provision of the specialized procedure. In such a case, the method may further include the step of collecting information relative to costs charged by the one of the plurality of first sites that has a smallest second site to first site travel related parameter. As this nearest first site may charge more than a first site that has a greater second site to first site travel related parameter, the price quote actually presented to, e.g., a client, for the provision of the specialized service may include a price quote for at least one of the first sites (as opposed to strictly for the first site having a smallest second site to first site travel related parameter).

A related apparatus may comprise a first site location information item (e.g., a piece of data, pieces of data, a collection of data, a database, as but a few examples) that includes information as to the location of at least one first site capable of performing a specialized procedure relative to individuals affiliated with a second site (e.g., the specialized procedure, such as testing, whether drug or clinical, may be performed on these individuals); a data receipt element (e.g., a computer keyboard and any necessary computer componentry) capable of receiving information relative to the location of said second site; mapping software (MapPoint as but one example) capable of accessing the first site information item; and a nearest first site location determination actuation element that actuates an automatic determination of a location of one of said at least one first site that has a smallest second site to first site travel related parameter. The second site has a location that is different from said location of the at least one first site. The nearest first site location determination actuation element may also actuate an automatic determination of a location of at least one additional first site that has an acceptable second site to first site travel related parameter (which may be, e.g., a second smallest second site to first site travel related parameter). The travel related parameter may be a drive time or a distance radius, as but two examples. The mapping software (e.g., MapPoint) capable of accessing said first site information item may do so by accessing at least one database of first site location information items. Further, regardless of whether the administration apparatus is a drug testing administration apparatus or a clinical testing administration apparatus, the apparatus may comprise a quote generation element which may be used to generate a quote based on first site locations determined using the apparatus.

At least one embodiment of the invention may also disclose a collection site locating facilitation feature (that itself may employ MapQuest®) accessible and usable on the internet or other electronic communicative medium, which may be usable to assist certain persons, such as the client (sponsoring entity) or collection site, e.g., in locating a certain collection site. Such provision may not only increase efficiency of the process (e.g., quoting), but also reduce the frequency of "no results" attributable to an inability of the donor to locate the collection site. If a certain site is unavailable to a donor, then the collection site locating facilitation feature may be used to determine where the collection site is.

As can be easily understood from the foregoing, the basic concepts of the present invention may be embodied in a variety of ways. It involves both identification, computerized form generation, and geographically related administration techniques as well as devices to accomplish these. In this application, the various techniques are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this nonprovisional application is intended to serve as a basic description. The reader should be aware that the specific discussion may not explicitly describe all embodiments possible; many alternatives are implicit. It also may not explicitly show how each feature or element can actually be representative of a broader function or of a great variety of alternative or equivalent elements. Again, these are, at the very least, implicitly included in this disclosure. Where the invention is described in device-oriented terminology, each element of the device implicitly performs a function. Apparatus claims may not only be included for the device described, but also method or process claims may be included to address the functions the invention and each element performs. Neither the description nor the terminology is intended to limit the scope of the claims.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon when drafting the claims for any subsequent patent application. This application is designed to yield a patent covering numerous aspects of the invention both independently and as an overall system.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of an "identifier" should be understood to encompass disclosure of the act of "identifying"—whether explicitly discussed or not—and, conversely, were there effectively disclosure of the act of "identifying", such a disclosure should be understood to encompass disclosure of an "identifier" and even a "means for identifying" Such changes and alternative terms are to be understood to be explicitly included in the description.

Any acts of law, statutes, regulations, or rules mentioned in this application for patent; or patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. Finally, all references listed in the list of References To Be Incorporated By Reference In Accordance With The Patent Application or other information statement filed with the application are hereby appended and hereby incorporated by reference, however, as to each of the above, to the extent that such information or statements incorporated by reference might be considered inconsistent with the patenting of this/these invention(s) such statements are expressly not to be considered as made by the applicant(s) or assignee.

Thus, the applicant(s) should be understood to have support to claim and make a statement of invention to at least: i) each of the identification, computerized form generation, and geographically related administration devices as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) each system, method, and element shown or described as now applied to any specific field or devices mentioned, x) methods and apparatuses substantially as described hereinbefore and with reference to any of the accompanying examples, xi) the various combinations and permutations of each of the elements disclosed, and xii) each potentially dependent claim or concept as a dependency on each and every one of the independent claims or concepts presented.

In addition, and as to computer aspects and each aspect amenable to programming or other electronic automation, the applicant(s) should be understood to have support to claim and make a statement of invention to at least: xii) processes performed with the aid of or on a computer as described throughout the above discussion, xiv) a programmable apparatus as described throughout the above discussion, xv) a computer readable memory encoded with data to direct a computer comprising means or elements which function as described throughout the above discussion, xvi) a computer configured as herein disclosed and described, xvii) individual or combined subroutines and programs as herein disclosed and described, xviii) the related methods disclosed and described, xix) similar, equivalent, and even implicit variations of each of these systems and methods, xx) those alternative designs which accomplish each of the functions shown as are disclosed and described, xxi) those alternative designs and methods which accomplish each of the functions shown as are implicit to accomplish that which is disclosed and described, xxii) each feature, component, and step shown as separate and independent inventions, and xxiii) the various combinations and permutations of each of the above.

With regard to claims presented for examination, it should be understood that for practical reasons and so as to avoid great expansion of the examination burden, the applicant or assignee may at any time present only initial claims or perhaps only initial claims with only initial dependencies. Support should be understood to exist to the degree required under new matter laws—including but not limited to European Patent Convention Article 123(2) and United States Patent Law 35 USC 132 or other such laws—to permit the addition of any of the various dependencies or other elements presented under one independent claim or concept as dependencies or elements under any other independent claim or concept. In drafting any claims at any time whether in this application or in any subsequent application, it should also be understood that the applicant or assignee has intended to capture as full and broad a scope of coverage as legally available. To the extent that insubstantial substitutes are made, to the extent that the applicant or assignee did not in fact draft any claim so as to literally encompass any particular embodiment, and to the extent otherwise applicable, the applicant or assignee should not be understood to have in any way intended to or actually relinquished such coverage as the applicant or assignee simply may not have been able to anticipate all eventualities; one skilled in the art, should not be reasonably expected to have drafted a claim that would have literally encompassed such alternative embodiments.

Further, if or when used, the use of the transitional phrase "comprising" is used to maintain the "open-end" claims herein, according to traditional claim interpretation. Thus, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant or assignee the broadest coverage legally permissible.

Finally, any claims set forth at any time are hereby incorporated by reference as part of this description of the invention, and the applicant or assignee expressly reserves the right to use all of or a portion of such incorporated content of such claims as additional description to support any of or all of the claims or any element or component thereof, and the applicant or assignee further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. A specimen identification method comprising the steps of:
   identifying a specimen donor with a specimen donor identification information item;
   adequately specifying a specimen related event identifier;
   associating said specimen donor identification information item with said specimen related event identifier;
   generating a unique specimen identification information item in response to said step of associating said specimen donor identification information item with said specimen related event identifier;
   rendering said specimen donor identification information item not immediately discernible;
   associating a discernment process specificity information item with said not immediately discernible specimen donor identification information item; and
   associating a character-based discernment code with said discernment process specificity information item to create a code representation information item, wherein said character-based discernment code represents said discernment process specificity information item.

2. A specimen identification method as described in claim 1 further comprising the step of associating said character-based discernment code with said unique specimen identification information item.

3. A specimen identification method as described in claim 2 wherein said step of associating said character-based discernment code with said unique specimen identification information item comprises the step of visually associating.

4. A specimen identification method as described in claim 3 wherein said step of generating a unique specimen identification information item comprises the step of generating a unique specimen identification information item that comprises said character-based discernment code.

5. A specimen identification method as described in claim 1 further comprising the step of limiting access to said code representation information item.

6. A specimen identification method comprising the steps of:
identifying a specimen donor with a specimen donor identification information item;
adequately specifying a specimen related event identifier;
associating said specimen donor identification information item with said specimen related event identifier;
generating a unique specimen identification information item in response to said step of associating said specimen donor identification information item with said specimen related event identifier; and
rendering said specimen donor identification information item not immediately discernible,
wherein the step of rendering said specimen donor identification information item not immediately discernible comprises the step of encrypting said specimen donor identification information item to create an encrypted specimen donor identification information item.

7. A specimen identification method as described in claim 6 further comprising the step of associating a decryption algorithm specificity information item with said encrypted specimen donor identification information item, wherein said decryption algorithm specificity information item is usable to decrypt said encrypted specimen donor identification information item.

8. A specimen identification method as described in claim 7 further comprising the step of associating a character-based decryption code with said decryption algorithm specificity information item to create a code representation information item, wherein said character-based discernment code represents said decryption algorithm specificity information item.

9. A specimen identification method as described in claim 8 further comprising the step of associating said character-based discernment code with said unique specimen identification information item.

10. A specimen identification method as described in claim 9 wherein said step of associating said character-based discernment code with said unique specimen identification information item comprises the step of visually associating.

11. A specimen identification method as described in claim 10 wherein said step of generating a unique specimen identification information item comprises the step of generating a unique specimen identification information item that comprises said character-based decryption code.

12. A specimen identification method as described in claim 8 or 11 further comprising the step of limiting access to code representation information item.

13. A specimen identification method as described in claim 7 further comprising the step of limiting access to said code representation information item.

14. A specimen identification method comprising the steps of:
identifying a specimen donor with a specimen donor identification information item;
adequately specifying a specimen related event identifier;
associating said specimen donor identification information item with said specimen related event identifier;
generating a unique specimen identification information item in response to said step of associating said specimen donor identification information item with said specimen related event identifier; and
rendering said specimen related event identifier not immediately discernible,
wherein the step of rendering said specimen related event identifier not immediately discernible comprises the step of encrypting said specimen related event identifier to create an encrypted specimen related event identifier.

15. A specimen identification method comprising the steps of;
identifying a specimen donor with a specimen donor identification information item;
adequately specifying a specimen related event identifier;
associating said specimen donor identification information item with said specimen related event identifier; and
generating a unique specimen identification information item in response to said step of associating said specimen donor identification information item with said specimen related event identifier,
wherein the step of generating a unique specimen identification information item comprises the step of generating a unique specimen identification information item that is not immediately discernible, and
wherein the step of generating a unique specimen identification information item that is not immediately discernible comprises the step of generating an encrypted specimen identification information item.

16. A specimen identification method as described in claim 15 further comprising the step of associating a decryption algorithm specificity information item with said encrypted specimen identification information item, wherein said decryption algorithm specificity information item facilitates decryption of said encrypted specimen identification information item.

17. A specimen identification method as described in claim 16 further comprising the step of associating a character-based, decryption code with said decryption algorithm specificity information item to create a code representation information item.

18. A specimen identification method as described in claim 17 further comprising the step of associating said character-based discernment code with said encrypted specimen identification information item.

19. A specimen identification method as described in claim 18 wherein said step of associating said character-based discernment code with said encrypted specimen identification information item comprises the step of visually associating.

20. A specimen identification method as described in claim 19 further comprising the step of establishing said character-based, decryption code as part of said encrypted specimen identification information item.

21. A specimen identification method as described in claim 17 or 19 further comprising the step of limiting access to said code representation information item.

22. A specimen identification apparatus comprising:
   a specimen donor identification information item associated with a specimen to be identified; and
   a specimen related event identifier associated with said specimen and appearing with said specimen donor identification information item so as to establish a specimen identifier,
wherein said specimen donor identification information item is not immediately discernible
wherein said not immediately discernable specimen donor identification information item has associated with it a discernment process specificity information item,
   said apparatus further comprising:
   a code representation information item in which said discernment process specificity information item has associated with it a character-based discernment code that represents said discernment process specificity information item.

23. A specimen identification apparatus as described in claim 22 wherein said character-based discernment code is visually associated with said specimen identifier.

24. A specimen identification apparatus comprising:
   a specimen donor identification information item associated with a specimen to be identified; and
   a specimen related event identifier associated with said specimen and appeasing with said specimen donor identification information item so as to establish a specimen identifier,
wherein said specimen donor identification information item is not immediately discernible,
wherein said not immediately discernable specimen donor identification information item is an encrypted specimen donor identification information item, and
wherein said encrypted specimen donor identification information item has associated with it a decryption algorithm specificity information item tat facilitates decryption of said encrypted specimen donor identification information item.

25. A specimen identification apparatus as described in claim 24 further comprising a code representation information item in which said decryption algorithm specificity information item has associated with it a character-based decryption code that represents said decryption algorithm specificity information item.

26. A specimen identification apparatus as described in claim 25 wherein said character-based discernment code is associated with said specimen identifier.

27. A specimen identification apparatus as described in claim 26 wherein said character-based discernment code is visually associated with said specimen identifier.

28. A specimen identification apparatus as described in claim 27 wherein said specimen identifier further comprises said character-based discernment code.

29. A specimen identification apparatus comprising:
   a specimen donor identification information item associated with a specimen to be identified; and
   a specimen related event identifier associated with said specimen and appearing with said specimen donor identification information item so as to establish a specimen identifier,
wherein specimen related event identifier is not immediately discernible,
wherein not immediately discernible specimen related event, identifier is an encrypted specimen related event identifier, and
wherein said encrypted specimen related event identifier has associated with it a decryption algorithm specificity information item that facilitates decryption of said encrypted specimen related event identifier.

30. A specimen identification apparatus as described in claim 29 further comprising a code representation information item in which said decryption algorithm specificity information item has associated with it a character-based decryption code that represents said decryption algorithm specificity information item.

31. A specimen identification apparatus as described in claim 30 wherein said character-based discernment code is associated with said specimen identifier.

32. A specimen identification apparatus as described in claim 31 wherein said character-based discernment code is visually associated with said specimen identifier.

33. A specimen identification apparatus as described in claim 30 wherein said specimen identifier further comprises said character-based decryption code.

34. A specimen identification apparatus comprising:
   a specimen donor identification information item associated with a specimen to be identified; and
   a specimen related event identifier associated with said specimen and appearing with said specimen donor identification information item so as to establish a specimen identifier,
wherein said specimen identifier is not immediately discernable,
wherein said not immediately discernable specimen identifier is an encrypted specimen identifier, and
wherein said encrypted specimen identifier has associated with it a description algorithm specificity information item that facilitates decryption of said encrypted specimen identifier.

35. A specimen identification apparatus as described in claim 34 further comprising a code representation information item in which said description algorithm specificity information item has associated with it a character-based decryption code that represents said decryption algorithm specificity information item.

36. A specimen identification apparatus as described in claim 35 wherein said character-based decryption code is associated with said encrypted specimen identifier.

37. A specimen identification apparatus as described in claim 36 wherein said character-based decryption code is visually associated with said encrypted specimen identifier.

38. A specimen identification apparatus as described in claim 37 wherein said encrypted specimen identifier comprises said character-based decryption code.

* * * * *